United States Patent [19]

Delente

[11] Patent Number: 5,327,901

[45] Date of Patent: * Jul. 12, 1994

[54] APPARATUS FOR COLLECTING AND STORING HUMAN BREATH SAMPLES

[75] Inventor: Jacques J. Delente, Kensington, Md.

[73] Assignee: Martek Biosciences Corporation, Columbia, Md.

[*] Notice: The portion of the term of this patent subsequent to May 18, 2010 has been disclaimed.

[21] Appl. No.: 52,621

[22] Filed: Apr. 27, 1993

Related U.S. Application Data

[63] Continuation-in-part of Ser. No. 702,022, May 17, 1991, Pat. No. 5,211,181.

[51] Int. Cl.$^5$ .............................................. A61B 5/097
[52] U.S. Cl. ...................................... 128/730; 422/84
[58] Field of Search ................ 128/716, 719, 727–730; 73/863.71–863.72, 864.55, 864.63; 422/84

[56] References Cited

U.S. PATENT DOCUMENTS

| | | | |
|---|---|---|---|
| 894,337 | 7/1908 | Morris | 128/727 |
| 3,321,976 | 5/1967 | Jones | 128/730 |
| 3,817,108 | 6/1974 | Principe et al. | 128/730 X |
| 5,211,181 | 5/1993 | Delente | 128/730 |

Primary Examiner—Angela D. Sykes
Attorney, Agent, or Firm—Rothwell, Figg, Ernst & Kurz

[57] ABSTRACT

A simplified, user-friendly method and apparatus for producing and collecting a human breath sample, and particularly alveolar air, for analysis of the constituent components thereof. The invention includes an elongated, hollow container and a breath delivery device for directing a subject's breath into the container. Closure means are provided for accommodating the insertion of the breath delivery device into the container and for substantially sealing the container. In one preferred embodiment, the closure means includes a flexible sealing element which allows the insertion and withdrawal of the breath delivery device and which forms a light interim seal at the opening of the hollow container while the opening is being positively sealed by the user. The volume of the container is small in comparison to the normal human breath which has the effect of purging the container of the initial breath portion and leaving primarily only the alveolar air.

6 Claims, 5 Drawing Sheets

APPARATUS FOR COLLECTING AND STORING HUMAN BREATH SAMPLES

CROSS-REFERENCE TO RELATED APPLICATION

This application is a continuation-in-part of application Ser. No. 07/702,022, filed May 17, 1991.

BACKGROUND OF THE INVENTION

1. Field of the Invention

This invention relates generally to a method and apparatus for collecting breath samples from humans and, in particular, is directed to an uncomplicated, user-friendly and relatively inexpensive apparatus and method for collecting such breath samples such that they consist primarily of alveolar gas as expelled from the pockets of the lungs.

2. Description of the Prior Art

Certain diagnostic techniques require analysis of the breath of a human subject to determine whether the breath contains a particular chemical compound, such as ethyl alcohol, carbon dioxide or ammonia, or a non-chemical, such as a particular microorganism. Determining the constituent components of the breath is best accomplished by analyzing the alveolar gas, that is the portion of the exhaled breath which is expelled from the air pockets of the lungs. In exhalation, as the lungs contract, breath contained in the mouth, throat and bronchials is necessarily exhaled first, followed by the breath contained in the alveoli of the lungs. Since it is at the alveoli where the exchange of substances between breath and blood ultimately occurs, the concentration of gaseous or vaporous constituents in the alveoli corresponds more closely to the concentration of substances dissolved in the blood. Thus, if a sample of breath is to be analyzed for the presence of constituents which may be present in the blood, the sample of breath analyzed must be at least primarily alveolar gas.

The equipment commonly used for collecting alveolar breath samples consists of bags, valves, syringe and needles and evacuated containers such as used for blood samples. These devices are expensive and complex which makes them very difficult for a patient to use. For example, U.S. Pat. No. 3,734,692 discloses an alveolar breath sampling apparatus utilizing a complicated compartmentalized bag having first and second inflatable regions. A dual channeled delivery port is constructed into the apparatus and communicates with both regions. The breath sample is collected by breathing into the delivery port resulting in the sequential collection in each region. This device is unnecessarily complex and expensive to construct.

In another known arrangement, the alveolar air portion of a person's breath is separated in response to the temperature of the conveyed air. For example, U.S. Pat. No. 4,248,245 discloses a method and device for separating alveolar air which includes conveying the exhaled air through a conduit and continuously monitoring the temperature of the conveyed air. When the variation in measured temperature drops below a threshold value, the air is directed into a measuring chamber. This device is also excessively complex and expensive to manufacture.

In still another prior art arrangement, two separate collection bags are used interconnected by a conduit. For example, in U.S. Pat. No. 3,544,273, a first collection bag and a second collection bag are connected by a T-shaped conduit having one branch formed into a mouth piece. The breath sample is collected by inflating the first bag with the initial breath portion and filling the second bag will the alveolar air. The second bag is sealed by using a valve structure. The complexity of these devices and resultant difficulty individual users have in operating them has often resulted in less than accurate measurements. In addition, such prior art systems are intimidating to the user and difficult to use in any event and thus are not as widely used as considered medically prudent for early diagnostic purposes.

Thus, there is a great need for an accurate, inexpensive and most importantly user friendly method and apparatus for collecting a human breath sample, primarily the alveolar portion thereof, for the analysis of the constituent components thereof.

SUMMARY OF THE INVENTION

Accordingly, the present invention provides, in one embodiment thereof, an inexpensive and user-friendly method and apparatus for collecting a human breath sample. In a preferred embodiment, the apparatus comprises an elongated, rigid hollow tubular container having an elongated chamber formed therein. One end of the elongated chamber is closed and the opposite end thereof is provided with an inlet portion forming an opening from the exterior to the interior of the chamber. An elongated, hollow delivery device is also provided which is designed to be inserted into the inlet portion of the chamber and to extend to near the closed end thereof for delivering a breath sample from a subject's mouth to the chamber. A closure means is also provided for substantially sealing the chamber after the breath sample has been collected and the delivery device has been removed from the chamber. The closure means is operable in a first position which accommodates the insertion of the delivery device and a in second position which substantially seals the chamber, thereby trapping and sealing the breath sample in the chamber such that the container can be transported to another location for analysis of the breath sample.

The volume of the elongated chamber is substantially smaller than the volume of a breath sample normally expelled by a human subject such that the exhalation of the breath into the chamber through the breath delivery device purges the chamber of the initial portion of the breath and leaves only primarily the alveolar portion of the expelled breath which is expelled later in the exhalation event.

In another preferred embodiment, a first closure means formed of a flexible material is affixed to the opening of the container and has formed therein one or more slits forming flap portions which are closely adjacent to each other and which preferably touch each other along the edges thereof to form a loose seal over the opening of the container. The flap portions are sufficiently flexible such that they can be flexed to permit the insertion and withdrawal of the breath delivery means with the application of only a slight force. With the breath delivery device inserted in the container through the flap portions, the spaces formed between the flap portions and the breath delivery device are sufficient to allow the purging expulsion of breath from the container through such spaces when the breath sample is discharged into the container through the delivery device.

In this embodiment, when the delivery device is withdrawn from the container through the flap portions, the flap portions return to their equilibrium position and form a light or loose seal of the opening of the container until a second closure means in the form of a sealing cap is placed over the opening and secured in place to form a positive seal.

BRIEF DESCRIPTION OF THE DRAWINGS

FIG. 1A is an exploded view of a portion of the embodiment of FIG. 1 showing a closure cap means for providing a further seal of the apparatus;

DETAILED DESCRIPTION OF THE PREFERRED EMBODIMENT

Figure 1:
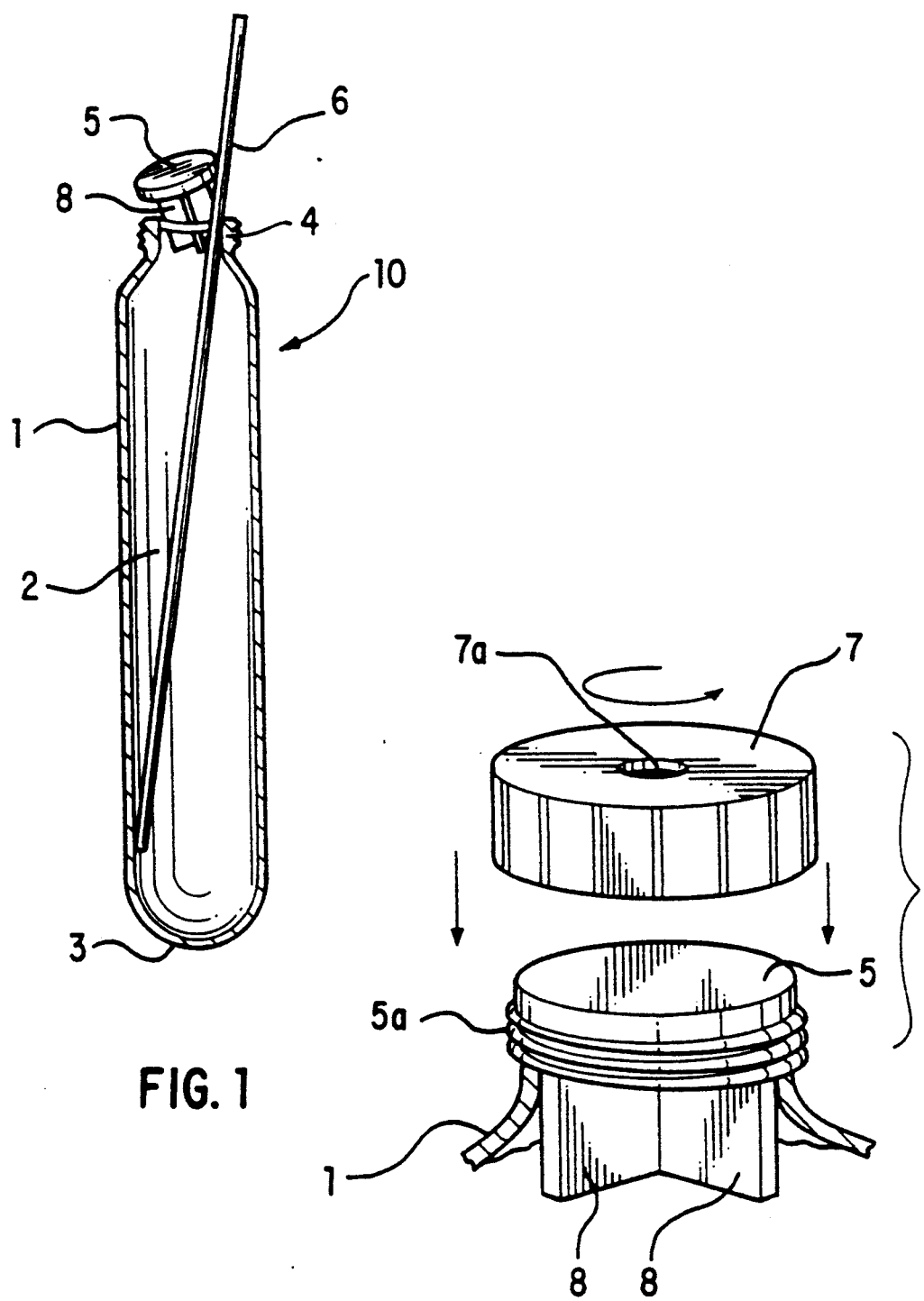
FIG. 1 is a front elevational view of a breath collection apparatus according to a first embodiment of the present invention.

The breath collection apparatus of the present invention will be discussed in detail with reference to FIG. 1 which shows breath collection apparatus 10 including an elongated, hollow, rigid tubular container 1 having an elongated, hollow chamber 2 therein. The elongated container 1 has a closed end 3 and an opposite end thereof having an inlet portion 4 forming an opening to the interior of chamber 2. The elongated tubular container can be any suitable closeable container. In a preferred embodiment, the tubular container is a common commercially available vial or test tube which forms the elongated, hollow chamber 2 which has a length substantially greater than its diameter.

The breath collection apparatus of FIG. 1 further includes an elongated, hollow breath delivery means 6 for delivering a breath sample from a subject's mouth into the chamber 2. The breath delivery means can be any suitable, preferably hollow, device which will facilitate directing a subject's exhaled breath into the container's interior chamber. In a preferred embodiment, the breath delivery means is a common commercially available plastic or glass straw.

The embodiment of FIG. 1 also includes closure means 5 for closing and substantially sealing the inlet portion 4 of the elongated container 1. The closure means 5 operates in at least two different positions. In a first position, the closure means accommodates the insertion of the breath delivery means into the container's interior chamber 2 as is illustrated in FIG. 1. In a second position, the closure means substantially seals the inlet portion 4 of the container 1. In the embodiment shown in FIG. 1, the closure means is placed in the second position to seal the inlet portion 4 after the removal of the delivery means 6.

The closure means 5 is adapted to removably seal the inlet portion of the elongated container 1 and to accommodate the insertion of the delivery means 6 in a manner such that the opening into the chamber 2 is at least partially covered during the use of the delivery means 6. In a preferred embodiment, the closure means 5 is formed of a resilient material, such as butyl rubber, and is shaped in the form of a disk 5 with one or more projecting blades 8 extending therefrom. The blades 8 provide means for facilitating positioning of the closure means into the first and second positions and for accommodating the insertion of the breath delivery means 6.

In a preferred embodiment as shown in FIG. 1A, a threaded screw cap 7 with a central hole 7a therein is mounted over closure means 5 and in threaded engagement with threads 5a on the tubular container 1 to press the disk 5 against the rim of the tubular container and assure a safe seal. The screw cap 7 is mounted after the closure means has substantially sealed the breath sample in the container 1 and provides a further seal for facilitating storage, moving and shipping of the sealed container. The hole 7a in the cap 7 is adapted to permit a sampling needle to be inserted into the sealed breath sample within the chamber 2 to withdraw a portion of the sample without removing the screw cap 7.

The method of collecting a breath sample utilizing the device shown in FIG. 1, according to the present invention, will be described as follows. The individual subject is instructed, preferably by instructions included with the apparatus, to place the closure means in a first position forming an opening at the inlet 4 and to insert the breath delivery means into the container through the opening so formed. The closure means is positioned in such a way that it partially rides over the breath delivery means. The delivery means 6 is preferably inserted such that the end thereof extends well into the chamber 2 and toward the closed end 3 thereof. The subject then exhales one normal breath through the delivery means into the chamber 2. Toward the end of the breath exhalation, the individual pulls the delivery means out of the inlet portion 4 of the container and places the closure means in its second position, substantially sealing the breath sample in the chamber 2.

The volume of elongated container 1 is substantially smaller than the volume of a normal exhaled breath. This comparatively small volume is provided so that as the subject exhales his or her breath through the breath delivery means, the initial portion of the expiration is purged from the interior chamber 2 through the inlet portion 4. Near the end of expiration, substantially only the alveolar air will remain which is then sealed in the container by closure means 5. The screw cap 7 is then screwed on and tightened to provide a further seal.

The elongated container 1 can be of any suitable size which will facilitate purging the initial portion of the expired breath from the container. In a preferred embodiment, the container is a serum bottle or vial made of glass with an inlet portion having a diameter ranging from about 10 mm to about 25 mm and having a total volume ranging from about 5 ml to about 100 ml.

The method and apparatus for collecting a human breath sample according to the present invention have many advantages over the prior art breath collection systems. The breath collection device 10 comprises very few elements and is inexpensive and easily constructed. Most importantly, because device 10 is so uncomplicated, it is very user-friendly, and the ease of use results in fewer user errors and improves the accuracy of the ultimate breath constituent analyses.

Another advantage of the present invention is its amenability to automated analysis. The slotted freeze drying stoppers 5, used in the preferred embodiment, can easily be pierced by a sampling needle, such as for automated injection into a gas isotope ratio mass spectrometer, or a gas chromatograph hydrogen analyzer. As noted above, the central hole 7a in the screw cap 7 allows the sampling needle to operate without having to remove the screw cap. The subject or patient can self administer the sampling without assistance at home as well as in the physician's office. All items are easily and conveniently incorporated in a diagnostic test kit. No syringes or needles (which represent a possible health risk) are required.

Figure 2:
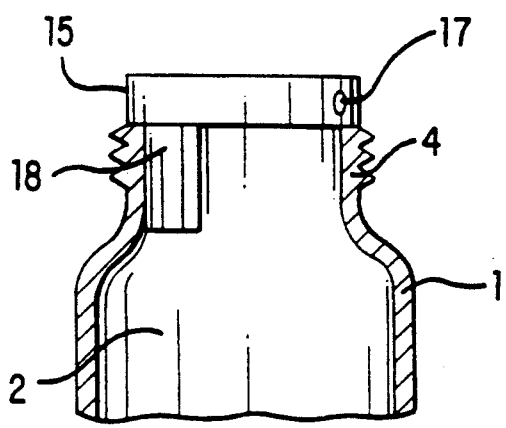
FIG. 2 is a cross-sectional view of the closure means in accordance with a second embodiment of the present invention.
Figure 3:
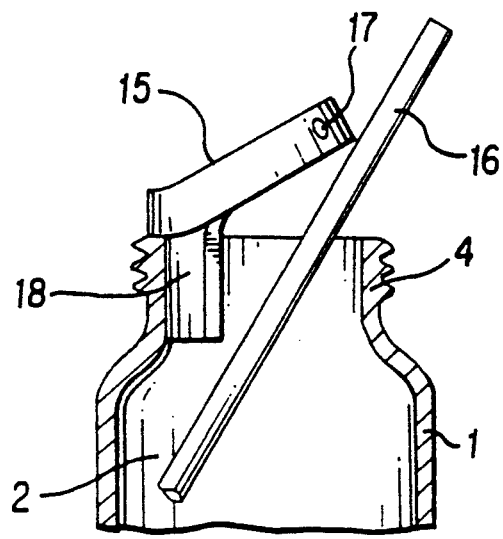
FIG. 3 is a cross-sectional view of the closure means shown in FIG. 2.
Figure 4:
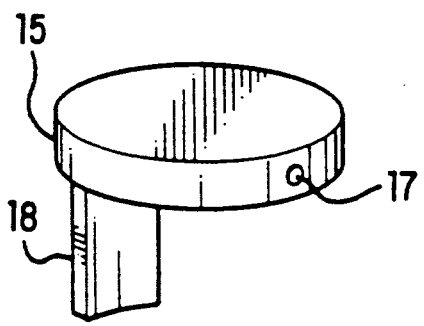
FIG. 4 is an enlarged top elevational view of the closure means shown in FIG. 2.

FIGS. 2-4 illustrate a second embodiment of the present invention. In this embodiment, a disk shaped closure means 15 is formed with a flexible projection 18 (formed, for example, of butyl rubber) which is affixed to the inside of the inlet portion 4 of the elongated container 1. Because the closure means is fixed to the container, handling and operating the breath collection device is greatly facilitated. The possibility of mishandling or losing the closure is essentially eliminated. The projection 18 can be affixed to the container by any suitable means, such as glue. In a preferred embodiment, the projection 18 is lined on one face with PTEE (Kimble Cat.# 73816-15) is glued by putting a very small droplet of Superglue TM (Cyanoacrylate made by The Loctite Co.) on the rim of the rubber face of the disk, and pressing onto the rim of a Borosilicate glass disposable screw cap culture tube. Closure means 15 is also constructed with a dot or marker, illustrated at 17, which indicates where the device should be lifted for inserting the breath delivery means. The marker is preferably positioned diametrically opposed to the place where the glue is applied.

FIG. 3 illustrates the closure means in the first position which accommodates the insertion of the breath delivery means 16. The individual user can very easily lift the stopper at marker 17 and will proceed to direct the breath sample into the chamber 2 using the breath delivery means. FIG. 2 illustrates the closure means in the second position, substantially sealing the container after the delivery means has been removed.

Figure 4A:
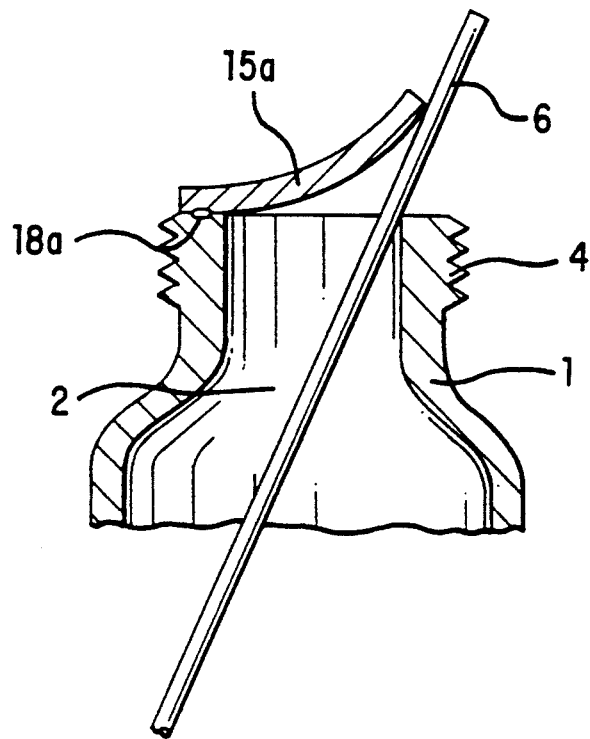
FIG. 4A is a cross-sectional view of a third embodiment of the invention.

In an alternative embodiment, the closure means can be provided without the projection 18 and can be affixed at one location to the rim of the inlet portion of the elongated container. Such an embodiment is shown in FIG. 4A. In this embodiment, a flexible preferably disk shaped closure means 15a is provided which is substantially similar to the portion 15 of the embodiment of FIGS. 2-4. The closure means 15a is secured at a single spot 18a on the periphery thereof to the periphery of the inlet portion 4 of the container 1. The single spot 18a is secured to the inlet portion 4 by a suitable adhesive in the same manner as described in the embodiment of FIGS. 2-4 in connection with the attachment of the projection 18. The flexible closure means 15a is normally flat as is the portion 15 of FIG. 2, and is resiliently urged into sealing engagement with the inlet portion 4 of the container 1. The closure means 15a can be flexed to an open position as shown in FIG. 4A to accommodate the insertion of the delivery means 6.

Figure 5:
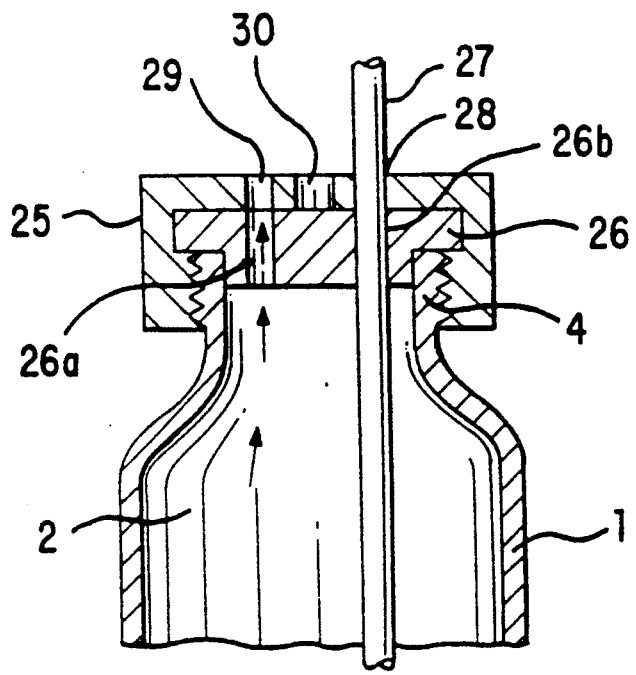
FIG. 5 is a cross-sectional view of a closure means in accordance with a fourth embodiment of the present invention.
Figure 6:
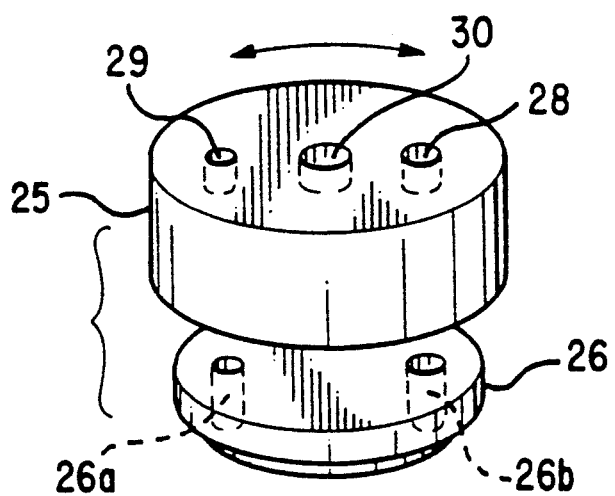
FIG. 6 is an enlarged top elevational view of the closure means shown in FIG. 5.

In still another embodiment of the present invention, FIGS. 5 and 6 illustrate a closure means which further facilitates using the breath collection device. A closure means 26 such as a device described in connection with FIG. 1 is positioned to substantially seal the inlet portion of the elongated container. The closure means has at least a first hole 26a and a second hole 26b formed therethrough which are positioned radially spaced from the center of the closure 26. A cap 25 is rotatably securable to the elongated container in any suitable manner, such as by threaded engagement therewith. Cap 25 has a first hole 28 and a second hole 29 formed therethrough which can be aligned with the first and second holes in the closure means 26 by rotating the cap 25 into a position of alignment, as illustrated in FIG. 5. The cap 25 also has a hole 30 extending therethrough at the center thereof to accommodate the insertion of a sampling needle without the necessity of removing the cap 25 after it has been secured in place in sealing engagement with the inlet portion 4 of the container 1.

The operation of the breath collection device of the embodiment of FIGS. 5 and 6 is as follows. The cap 25 is loosely secured on the inlet portion 4 of the container 1 and the individual subject rotates the cap 25 until the first hole 28 is aligned with the hole 26b in the closure means 26 and the second hole 29 is aligned with the hole 26a in the closure means 26. The respective positioning of the holes is such that these alignments occur at a single selected position of cap 25 relative to the closure means 26. The breath delivery means 27 is then inserted through one of the first or second holes 28 or 29 in cap 25 and into the interior chamber of the elongated container with the delivery means being positioned so that the end thereof extending into the chamber extends to a position near the closed end 3 of the chamber 2. For illustrative purposes, FIG. 5 shows breath delivery means 27 inserted into the first hole 28. The subject then exhales a normal breath through the breath delivery means 17 and into the chamber 2. Because of the small volume of the chamber 2 relative to the volume of a normal expelled human breath from a subject, the initial portion of the expiration will be purged through the second aligned holes 26a and 29 thereby leaving primarily only the alveolar portion of the expiration in the chamber 2. The cap 25 is then rotated so that the first and second holes are moved out of alignment thereby closing the paths into and out of the chamber 2. The cap 25 is tightened down on the closure means 26 to firmly seal the breath sample inside the chamber 2. FIG. 6 illustrates the alignment of the holes 28 and 29 in the cap 25 with the holes 26b and 26a of the closure means 26.

Figure 7:
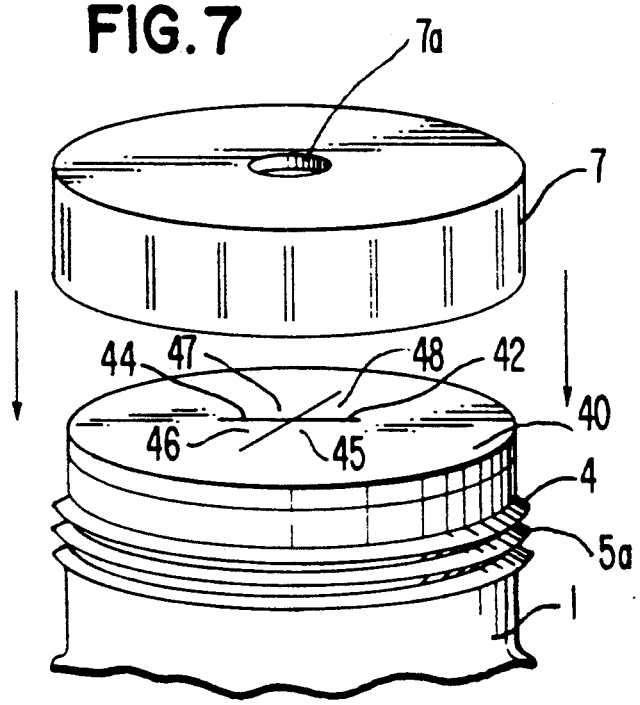
FIG. 7 is an exploded view, taken in perspective, of a portion of another embodiment of the present invention showing a first enclosure means for providing an interim seal of the breath sample container and a second enclosure means for providing a further positive seal thereof.
Figure 8:
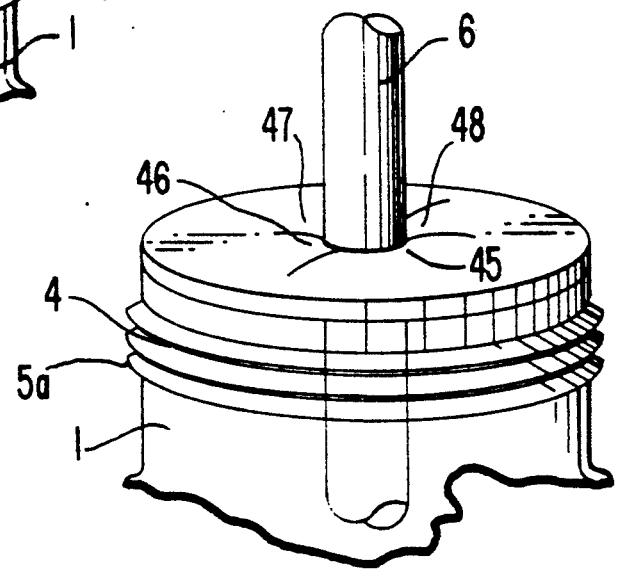
FIG. 8 is a perspective view of a portion of the embodiment of FIG. 7 showing a breath delivery device inserted through the first enclosure means.
Figure 9:
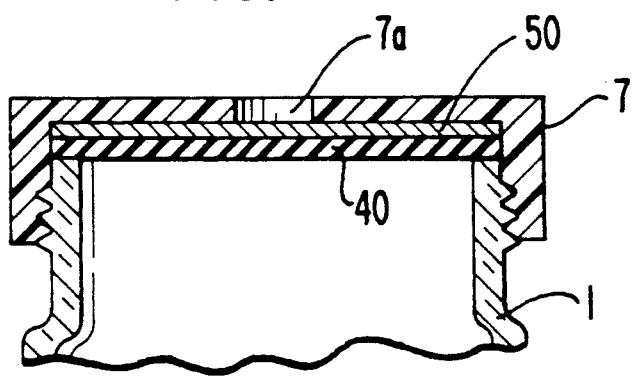
FIG. 9 is a cross sectional view of a portion of the embodiment of FIG. 7 showing the second enclosure means secured in place in positive sealing engagement.

FIGS. 7, 8 and 9 show still another embodiment of the present invention in which another preferred form of closure means is employed for closing the container 1. In this embodiment, a first closure means for closing and lightly sealing the opening of the inlet portion 4 includes a flexible sealing element 40, which is made of a flexible material such as synthetic rubber (e.g., butyl rubber), and which is secured, such as by means of a suitable adhesive, in sealing engagement with the top of the inlet portion 4 of the tubular container 1 as shown in FIG. 7.

The flexible sealing element 40 has cross slits 42 and 44 formed therein which form deflectable flap portions 45, 46, 47 and 48 which can be deflected to permit the insertion and withdrawal of the breath delivery means 6 in a manner later to be described. The outer periphery of the flexible sealing element 40 is firmly sealed to the opening of the inlet portion 4, preferably by means of an adhesive, so as to be substantially flush with the outer periphery thereof to permit the closure screw cap 7 to be threaded onto the inlet portion 4 in engagement with threads 5a to close and seal the opening of the inlet portion 4.

The breath delivery device 6 is inserted into the chamber 2 by lightly forcing the end of the delivery device through the slits 42 and 44 to deflect the flap portions 45-48. The flap portions 45-48 are sufficiently resilient so that they readily permit the insertion of the breath delivery device 6 through the slits 42 and 44 with only a slight force being applied but return to their equilibrium position to lightly seal the opening of the inlet portion 4 when the delivery device 6 is removed.

FIG. 8 shows the delivery device 6 in the inserted position with the flap portions 45-48 being deflected inwardly toward the inside of the hollow chamber 4. It has been found that, with the delivery device in the inserted position as shown in FIG. 8, there is sufficient space around the delivery device 6 at its contact with the flap portions 45-48 to accommodate the purging discharge of the initial portions of the breath sample from the hollow chamber 2 during the process of expelling a breath sample such that only the alveolar portion of the sample remains in the hollow chamber after the sample discharge has been completed. After the breath sample has been taken by the expelling of a full breath, the delivery device 6 is removed from the container 1 by withdrawing it through the slits 42 and 44 in a direction opposite to that employed for the insertion of the delivery device.

After the breath sample has been taken and the delivery device 6 has been removed from the slits 42 and 44, the resilience of the flap portions 45-48 causes them to return to their equilibrium position and form a light resilient seal at the opening of the inlet portion 4. This provides an interim seal until the cap 7 has been screwed into place to form a positive seal over the inlet portion 4.

Inserted within the cap 7 is a sealing layer element 50 which covers the opening 7a in the cap and which engages the peripheral edge of the opening of the inlet portion 4 to form a positive seal with the cap 7 when the cap 7 is screwed onto the threads 5a and firmly tightened in place as shown in FIG. 9. The sealing layer element is preferably disk shaped to fit snugly within the cap 7 so that it is retained within the cap as a sealing layer. As noted earlier, the hole 7a accommodates the insertion of a syringe to permit the withdrawal of a portion of the breath sample from the container 1. The cap liner element 50 is therefore preferably formed of a material that is relatively easily punctured by the needle of a sampling syringe.

FIG. 9 shows the apparatus with the cap tightened in place after a breath sample has been taken and stored within the container 1. As shown, the cap sealing layer element 50 provides a positive seal over the flexible sealing element 40 over the opening of the inlet portion 4 and is held firmly in place in positive sealing engagement by the cap 7.

It has been found that, after a breath sample has been taken in the manner just described and the breath delivery device 6 has been removed from the slits 42 and 44, the resilient flap portions 45-48 formed by the slits form a light seal which is fully effective for the short time period typically required for the user to place the cap 7 in place on the inlet portion 4.

The slits 42 and 44 may be formed by making one or more cuts in the flexible sealing element 40 with a sharp blade, or in any other suitable manner, such that virtually no material is removed and so that the edges of the flap portions 45-48 formed by the slits are closely adjacent to each other and preferably loosely touch each other after they are formed. Although two or more such slits are preferred, only one slit may be employed to form two such flap portions. The flexible sealing element 40 may be formed of any suitable flexible material such a synthetic rubber, for example butyl rubber.

The term "slits" as used herein refers to very thin or very fine cuts or openings in which the edges of the flap portions formed by the slits are closely adjacent to each other and preferably loosely touch each other at least along portions of the edges thereof to form a loose seal in their equilibrium position.

Figure 10:
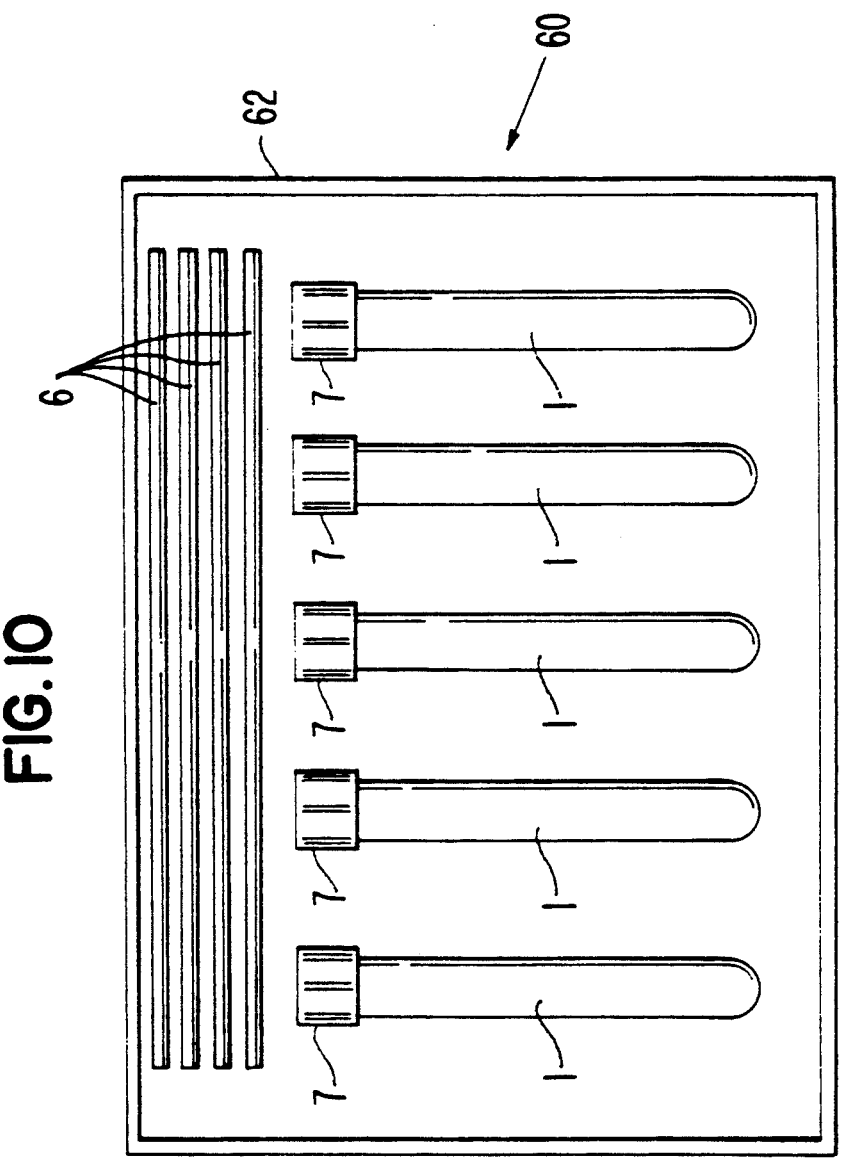
FIG. 10 is a plan view of the embodiment of FIGS. 7-9 packaged in kit form.

FIG. 10 shows a kit 60 in which a number of elements of the embodiment of FIGS. 7-9 are packaged together in a kit form. The elements are packaged in a box type container 62 which is shown with the cover removed. Positioned within the box container 62 are breath sample containers 1 with caps 7 fastened thereon. The breath sample containers 1 packaged in the kit 60 are of the type shown in FIGS. 7-9 and each such container 1 has a flexible sealing element 40 fastened and firmly sealed in place over the opening of the inlet portion 4 thereof.

Also packaged in the kit 60 are breath delivery devices 6, which can be inserted into the containers 1 through the slits 42 and 44 after the cap 7 has in each case been removed. The kit 60 is thus packaged to allow the user to take a number of separate breath samples, either at different times or under different conditions, and store them in the containers 1 for separate analysis.

Although the invention has been described in connection with certain embodiments, it is not limited to such embodiments. Modifications falling within the scope of the following claims will be apparent to those skilled in the art without departing from the true scope of applicant's invention as defined in the appended claims.

What is claimed is:

1. A breath sample collection apparatus for collecting and storing a human breath sample for analysis of the constituent components thereof, comprising:
   (a) an elongated, rigid hollow tubular container having an elongated chamber therein, one end of said container being closed and an opposite end thereof having and inlet portion forming an opening to the interior of said chamber;
   (b) a hollow breath delivery means for delivering a breath sample from a subject's mouth, said breath delivery means being insertable into said chamber through said inlet portion to deliver to said chamber a breath sample expelled from said subject's mouth, said chamber having a volume which is substantially less than the volume of a breath sample normally expelled by a human whereby said expulsion of said breath purges said chamber of an initial portion of said breath through said inlet portion leaving only primarily an alveolar portion of the expelled breath;

(c) a first closure means secured over the opening of said inlet portion for closing and lightly sealing said opening of said inlet portion, said first closure means being formed of a flexible sealing element having at least one slit therein forming flexible flap portions lightly sealing said inlet portion of said chamber, said flexible flap portions accommodating the insertion and removal of said breath delivery means and forming a space around said delivery means when the same is inserted which is sufficient to permit the purging expulsion of said initial portion of said breath; and (d) a second closure means for forming a positive seal of said inlet portion over said first closure means.

2. A breath collection apparatus as set forth in claim 1 wherein said second closure means comprises a cap adapted to be secured in sealing engagement on said inlet portion over said first closure means.

3. A breath collection apparatus as set forth in claim 2 wherein said cap includes an aperture formed therein covered with a sealing layer capable of being punctured by a needle of a syringe for withdrawing a breath sample from said container.

4. A breath sample collection kit for collecting and storing a human breath sample for analysis of the constituent components thereof, comprising:

(a) at least one elongated, rigid hollow tubular container having an elongated chamber therein, one end of said container being closed and an opposite end thereof having an inlet portion forming an opening to the interior of said chamber;

(b) at least one hollow breath delivery means for delivering a breath sample from a subject's mouth, said breath delivery means being insertable into said chamber through said inlet portion to deliver to said chamber a breath sample expelled from said subject's mouth, said chamber having a volume which is substantially less than the volume of a breath sample normally expelled by a human whereby said expulsion of said breath purges said chamber of an initial portion of said breath through said inlet portion leaving only primarily an alveolar portion of the expelled breath;

(c) a first closure means secured over the opening of said inlet portion for closing and lightly sealing said opening of said inlet portion, said first closure means being formed of a flexible sealing element having at least one slit therein forming flexible flap portions lightly sealing said inlet portion of said chamber, said flexible flap portions accommodating the insertion and removal of said breath delivery means and forming a space around said delivery means when the same is inserted which is sufficient to permit the purging expulsion of said initial portion of said breath; and (d) second closure means for forming a positive seal of said inlet portion over said first closure means.

5. A breath collection kit as set forth in claim 4 wherein said second closure means comprises a cap adapted to be secured in sealing engagement on said inlet portion over said first closure means.

6. A breath collection kit as set forth in claim 5 wherein said cap includes an aperture formed therein covered with a sealing layer capable of being punctured by a needle of a syringe for withdrawing a breath sample from said container.

* * * * *